United States Patent [19]

Sextl et al.

[11] Patent Number: 5,676,838
[45] Date of Patent: Oct. 14, 1997

[54] PROCESS FOR ISOLATING HYDROXYMONOCARBOXYLIC AND TRICARBOXYLIC ACIDS

[75] Inventors: Elfriede Sextl, Geiselbach; Akos Kiss; Heike Kinz, both of Hanau; Wiltrud Schaefer-Treffenfeldt, Obertshausen, all of Germany; Sems Yonsel, Istinye-Istanbul, Turkey; Stefan Stockhammer, Freigericht, Germany

[73] Assignee: Degussa Aktiengesellschaft, Frankfurt, Germany

[21] Appl. No.: 385,956

[22] Filed: Feb. 9, 1995

[30] Foreign Application Priority Data

Feb. 9, 1994 [DE] Germany ............... 44 03 987.5

[51] Int. Cl.$^6$ ................................. B01D 15/04

[52] U.S. Cl. ........................... 210/670; 210/691
[58] Field of Search ........................ 210/670, 691

[56] References Cited

U.S. PATENT DOCUMENTS

| 2,253,061 | 8/1941 | Cole .................... 260/535 |
| 2,882,244 | 4/1959 | Milton .................. 252/455 |
| 4,902,829 | 2/1990 | Kulprtahipanja ........ 562/580 |
| 5,312,980 | 5/1994 | Yonsel et al. .......... 562/554 |

*Primary Examiner*—Ivars Cintins
*Attorney, Agent, or Firm*—Cushman Darby & Cushman Ip Group of Pillsbury Madison & Sutro LLP

[57] ABSTRACT

The invention relates to the removal of hydroxymonocarboxylic acids and tricarboxylic acids from aqueous solutions by adsorption on zeolites with a modulus of up to 400.

14 Claims, No Drawings

PROCESS FOR ISOLATING HYDROXYMONOCARBOXYLIC AND TRICARBOXYLIC ACIDS

The invention relates to the removal of hydroymonocarboxylic and tricarboxylic acids from aqueous solutions by adsorption on zeolites.

Important acids of this type are citric and lactic acids, which are obtained in large amounts, mainly in fermentation processes.

The most effective method of purification for citric acid has been precipitation of relatively sparingly soluble calcium citrate. The pure acid is obtained from this salt by adding sulphuric acid and precipitating gypsum. Thus, for every ton of citric acid, about 2.5 t of by-product is produced, of which the greatest proportion, 65%, is gypsum.

The complex-forming properties of citric acid means that the solubility of gypsum and other organic salts in the operating solutions is about 10 times greater than in water. Direct evaporation of this solution, therefore, leads to large amounts of incrustations on heating units and piping systems, due to the deposition of gypsum. All modern processes therefore make use of at least one cation exchange stage in which calcium and other cations are replaced by hydrogen ions. The sulphate ions which are also present in solution may either be precipitated with barium carbonate or removed on an anion exchanger (Ullmanns Enzyklopädie, vol. 9, 4th ed. 1975, 632).

Removal of lactic acid from fermentation liquors and the associated purification procedure is also generally performed using anion and cation exchangers (EP-A 0 517 242, EP-A 0 393 818).

EP-A 0 442 181 discloses a prepulse process for separating saturated hydroxydicarboxylic acids from unsaturated dicarboxylic acids. In this case, the latter are more strongly adsorbed on a non-zeolitic silicon dioxide molecular sieve (silicalite) and thus separated from the saturated acid, in this case malic acid. Desorption is performed using an organic solvent/water mixture.

In accordance with the definition given in this application, silicalite has a modulus of ∞ since it is $Al_2O_3$-free.

The object of the invention is now to provide a simple separation process.

The invention provides a process for removing saturated hydroxymonocarboxylic acids and tricarboxylic acids from aqueous solution by adsorption, which is characterised in that an aqueous solution containing these carboxylic acids is brought into contact, under adsorption conditions, with an adsorbing material containing a zeolite, preferably with a modulus ($SiO_2/Al_2O_3$ ratio) of up to 400, and recovering the corresponding carboxylic acids therefrom by desorption. The initial solutions preferably arise from fermentation liquors produced during the production of these acids.

This process is preferably used for isolating citric acid and lactic acid or their alkali metal salts.

Adsorption conditions are understood to mean a pH range of 0.5 to 5, preferably 1 to 4.0, wherein the temperatures are generally in the range 15° to 50° C., preferably 20° to 30° C.

The zeolite may be used either in powder form in a suspension or in the granulated form or as moulded bodies (e.g. cylinders) in a fixed bed.

A dealuminised Y-zeolite (DAY) with a modulus in the range 20 to 400, preferably up to 250, has proved particularly suitable for the adsorption of citric acid. The pore diameter of dealuminised Y-zeolite is ca. 0.8 nm. This type of zeolite is known per se (Kirk-Othmer, The Encyclopedia of Chemical Technology, Third ed., vol. 15, 638–669).

Lactic acid is also adsorbed by this type of zeolite, also in particular, however, by zeolites of the ZSM-5 type or mordenite with a modulus between 15 and 400. All zeolites are preferably used in the H or Na form in this process.

Desorption of the adsorbed acids is performed by treating the separated solid bodies with an alkali metal hydroxide or ammoniacal solution. In the latter case, an $NH_3$ concentration of 0.1 to 3 g of $NH_3$/l of $H_2O$ is chosen and this solution is used in a ratio by weight of up to 10:1, with respect to the amount of zeolite. The desorption solution is preferably passed several times, for instance through a column full of zeolite. The corresponding salts of the acids are obtained in this way.

The pH drops with increasing release of the adsorbed acids, but should not undershoot the value of 5, in order to avoid renewed adsorption.

Taking this into account, it is also possible to desorb using neutral water. The pure acids are then obtained.

In adsorption/desorption trials with citric acid on DAY modulus 200, performed with a fixed bed column, it was shown that the absorption and desorption capacities remained constant, within the limits of the errors of measurement, over 10 cycles.

An advantage of the process according to the invention is also that the solutions arising during fermentative production of the acids may be used as the starting solutions, preferably after removing any solids which may be present, in particular, however, the biomass.

As is known, there is a certain spectrum of by-products and impurities which are frequently not specified in detail and which depend on the source of carbon. It has been shown that a good separating capacity can be achieved with mordenite for fermentation liquors with a molasses base, while zeolites of the DAY type, in particular DAY 200, enable good separation from glucose media (see Table 1).

By-products such as oxalic acid, fumaric acid or acetic acid can be specifically removed by treating the solutions with a zeolite of the ZSM-5 type, this being followed by adsorption of the acids which it is desired to produce on zeolites of the DAY or mordenite type.

EXAMPLE 1

Adsorption of Citric Acid

The following zeolites were used (H form, pore size ~0.8 nm)

| | |
|---|---|
| Wessalith®-DAY | modulus 200 |
| Wessalith®-DAY | modulus 110 |
| Wessalith®-DAY | modulus 56 |
| Wessalith®-DAY | modulus 25 |

Wessalith®-DAY—dealuminised Y-zeolite, from Degussa.

Test Conditions

Temperature: 25°±3° C.

Valuable product: citric acid solutions with concentrations of 0.5–30 wt. % citric acid pH: Conditions were used under which a pH of ca. 1–3 was produced on combining the citric acid and the zeolite Ratio of zeolite (abs. dry):product solution=1:10

Experimental Details

Citric acid solutions with different concentrations were each added to 5 g of DAY zeolite powder with the moduli 200, 110, 56 and 25 respectively and the suspensions shaken in conical flasks at room temperature. The reference samples of citric acid solutions contained no zeolite powder, but were shaken under the same conditions as the test solutions. The maximum equilibrium loads produced after analysis of the reference and equilibrium solutions are given in the following Table:

| Type of zeolite: | Maximum equilibrium load in g of citric acid per 100 g of DAY (abs. dry) |
|---|---|
| Wessalith DAY modulus 200 | 12 |
| Wessalith DAY modulus 110 | 8 |
| Wessalith DAY modulus 56 | 8 |
| Wessalith DAY modulus 25 | 6 |

Adsorption equilibrium was reached after a maximum of hours.

EXAMPLE 2

Adsorption and Desorption of Citric Acid

A zeolite of the Wessalith-DAY modulus 200 type was used in the form of 2 mm solid cylinders (DE-OS 42 02 671 and DE-OS 41 17 202).

Test Conditions

Temperature: 25°±3° C.

Valuable product: 12 wt. % citric acid solution

Ratio of zeolite:adsorption solution: 1:10

Ratio of zeolite:desorption solution: 1:10

Desorption solution: $NH_3$ solution with 1.0 g $NH_3$/l $H_2O$ pH during adsorption: 1–2 pH during desorption: ca. 11 (start)→ca. 5 (end)

Throughput of valuable product solution: 900 ml/h

Experimental Details

About 40 g of zeolite moulded bodies of the DAY modulus 200 type were placed in a fixed bed column. About 400 ml of citric acid solution (12% strength solution) were then pumped through this column for 2 hours in a circulating system. The equilibrium solution was analysed. After this adsorption procedure, the moulded bodies were washed with FD-$H_2O$, i.e. FD-$H_2O$ was pumped through the column in the circuit for 15 minutes. The wash water was also analysed (FD=fully deionised).

After the wash process, the desorption solution (about 400 ml) was pumped through the column in the circuit for 2 hours. The desorption solution was then analysed for citric acid content.

The adsorption/desorption cycles were repeated 10 times using this zeolite.

The adsorption capacity of the zeolite remained constant over 10 cycles and desorption was quantitative each time.

The X-ray diffraction diagram shows the crystallinity of the starting material after 10 cycles.

EXAMPLE 3

Adsorption of Lactic Acid

The following zeolites were used (H form):

| Wessalith DAY | modulus 200 |
|---|---|
| Wessalith DAY | modulus 110 |
| Wessalith DAY | modulus 56 |
| Wessalith DAY | modulus 25 |
| H-ZSM5 | modulus 400 |
| H-ZSM5 | modulus 42 |
| H-ZSM5 | modulus 28 |
| H-mordenite | modulus 30 |

Test Conditions

Temperature: 25°±3° C.

Valuable product: lactic acid solutions with concentrations of 1–25 wt. % of lactic acid pH: Conditions were used under which the combination of lactic acid and zeolite produced a pH of 1.5–3

Ratio of zeolite (abs. dry):valuable product solution: 1:10

Experimental Details 25 g of lactic acid solution of different concentrations were added to each 2.5 g of zeolite powder and the suspensions were shaken in conical flasks at room temperature. The reference samples of lactic acid solution contained no zeolite powder. The maximum equilibrium loads obtained are given in the following Table:

| Type of zeolite | Maximum equilibrium load in g of lactic acid per 100 g of zeolite (abs. dry) |
|---|---|
| DAY modulus 200 | 15 |
| DAY modulus 110 | 12 |
| DAY modulus 56 | 12 |
| DAY modulus 25 | 11 |
| H-ZSM-5 modulus 400 | 14 |
| H-ZSM-5 modulus 42 | 10 |
| H-ZSM-5 modulus 28 | 7 |
| H-mordenite modulus 30 | 5 |

The maximum equilibrium load for lactic acid adsorption was reached after a maximum of 1 hour.

EXAMPLE 4

Removal of Citric Acid from Fermentation Liquors

It was shown that the removal of citric acid (CIT) from fermentation liquors with different bases required the preferred use of different types of zeolite.

TABLE 1

| | Zeolite | Modulus | Load of CIT (%) | Load (%) of by-products | Purity on the zeolite (%) |
|---|---|---|---|---|---|
| Molasses base | DAY | 200 | 7.3 | 1.95 | 78 |
| | mordenite | 30 | 4.0 | 0 | 100 |
| Glucose base | DAY | 200 | 8.7 | 0.15 | 98 |
| | mordenite | 30 | 1.1 | 0.8 | 69 |

EXAMPLE 5

Adsorption of By-Products on ZSM-5 from a Fermentation Liquor

The following zeolite was used (H form)

| ZSM-5 | modulus 28 | 2 mm solid cylinders |
|---|---|---|

Test Conditions

Temperature: 25°±3° C.

Valuable product: Fermentation liquor (FL) with 5% citric acid, 0.5% oxalic acid, 0.5% fumaric acid pH: Conditions were used such that combination of FL and zeolite produced a pH of ca. 1–3

Ratio of zeolite (abs. dry):valuable product 1:3

Experimental Details 120 g of FL were added to 40 g of ZSM-5 zeolite moulded bodies (MB) and shaken in a conical flask at room temperature for 20 hours. The reference sample of FL contained no MB, but was shaken under the same conditions as the test solution.

Adsorption of the by-products tested increased with decreasing ZSM-5 modulus. The fumaric acid could be removed completely and the oxalic acid could be 70% removed from the adsorption solution with ZSM-5 modulus 28.

We claim:

1. A process for removing at least one carboxylic acid selected from the group consisting of hydroxymonocarboxylic acids and tricarboxylic acids from aqueous solution by adsorption, comprising the steps of contacting a solution containing at least one of these carboxylic acids, under adsorbing conditions, with an adsorbing material containing a zeolite selected from the group consisting of dealuminised Y zeolite with a modulus between 20 and 400 and zeolite of the ZSM-5 or mordenite type with a modulus between 15 and 400, and recovering the corresponding carboxylic acid therefrom by contacting the adsorbing material with a desorbing solution.

2. A process according to claim 1, wherein the aqueous solution contains citric acid.

3. A process according to claim 1, wherein the aqueous solution contains lactic acid.

4. A process according to claim 1, wherein the pH of the carboxylic acid solution is between 0.5 and 5 during adsorption.

5. A process according to claim 4, wherein the pH is between 1.0 and 4.0.

6. A process according to claim 1, wherein the carboxylic acid is desorbed with an aqueous desorbing solution and the pH during desorption is not less than 5.

7. A process according to claim 6, wherein the carboxylic acid is desorbed with an alkali metal hydroxide solution.

8. A process according to claim 6, wherein the carboxylic acid is desorbed with an ammoniacal solution.

9. The process according to claim 8, wherein the carboxylic acid is desorbed with an ammoniacal solution and the desorption starts at an initial pH of approximately 11.

10. The process according to claim 6 wherein water is a desorbing agent.

11. A process according to claim 1, wherein the carboxylic acids are produced by fermentation and the acids are removed from a fermentation broth produced thereby.

12. A process according to claim 11, wherein the carboxylic acids are removed from the fermentation broth, said broth having a glucose base.

13. A process according to claim 11, wherein the carboxylic acids are removed from the fermentation broth, said broth having a molasses base.

14. A process according to claim 11, wherein acetic acid, oxalic acid, and fumaric acid by-products of said fermentation are adsorbed on a zeolite of the ZSM-5 type before removing at least one of the hydroxymonocarboxylic acids and the tricarboxylic acids.

* * * * *